United States Patent [19]
Prota et al.

[11] Patent Number: 5,273,550
[45] Date of Patent: Dec. 28, 1993

[54] PROCESS AND KIT FOR DYEING HAIR

[75] Inventors: Giuseppe Prota, Naples, Italy; Leszek J. Wolfram, Stamford; Gottfried Wenke, Woodbridge, both of Conn.

[73] Assignee: Clairol Incorporated, New York, N.Y.

[21] Appl. No.: 766,606

[22] Filed: Sep. 26, 1991

[51] Int. Cl.$^5$ ............................................... A61K 7/13
[52] U.S. Cl. .................................... 8/405; 8/406; 8/407; 8/408; 8/409; 8/410; 8/414; 8/416; 8/423; 424/70
[58] Field of Search ............... 8/405, 406, 407, 408, 8/409, 410, 414, 416, 423; 424/70

[56] References Cited

U.S. PATENT DOCUMENTS

| | | | |
|---|---|---|---|
| 2,539,202 | 1/1951 | Peck | 8/10 |
| 2,934,396 | 4/1960 | Charle et al. | 8/10 |
| 3,194,734 | 7/1965 | Seemuller | 167/88 |
| 3,796,723 | 3/1974 | Kaiser et al. | 8/10 |
| 3,993,436 | 11/1976 | Fujinuma | 8/423 |
| 4,021,538 | 5/1977 | Yu et al. | 424/60 |
| 4,390,341 | 6/1983 | Jacobs | 8/406 |
| 4,453,941 | 6/1984 | Jacobs | 8/405 |
| 4,746,322 | 5/1988 | Herlihy | 8/405 |
| 4,776,857 | 10/1988 | Carroll et al. | 8/405 |
| 4,822,375 | 4/1989 | Lang et al. | 8/408 |
| 4,885,006 | 12/1989 | Grollier et al. | 8/406 |
| 4,904,274 | 2/1990 | Schultz et al. | 8/406 |
| 4,968,497 | 11/1990 | Wolfram et al. | 8/408 |
| 5,064,442 | 11/1991 | Grollier | 8/405 |
| 5,135,544 | 8/1992 | Grollier et al. | 8/405 |
| 5,173,085 | 12/1992 | Brown et al. | 8/406 |

FOREIGN PATENT DOCUMENTS 2132642 7/1984 United Kingdom .

OTHER PUBLICATIONS

K. Brown et al., J. Soc. Cosmet. Chem., 40:65–74 (1989) (no month available).
Prota, Med. Res. Rev., 8:525–56 (1988) (no month available).
Raper, Biochem. J., 89–96 (1927) (no month available).
Bu'Lock et al., J. Chem. Soc., 2248–52 (1951) (no month available).
Bu'Lock et al., nature, 166:1036–7 (1950) (no month available).
Mason et al., J. Biol. Chem., 180:235–47 (1949) (no month available).
Wakamatsu et al., Anal. Biochem., 170:335–40 (1988) (no month available).
Palumbo et al., Biochim. et Biophys. Acta, 925: 203–9 (1987) (no month available).
Beer et al., J. Chem. Soc., 1947–53 (1954) (no month available).
Napolitano et al., Gaz. Chim. Ital., 115:357–9 (1985) (no month available).
Crescenzi et al. Tetrahedron, 47:6243–50 (1991) (no month available).

*Primary Examiner*—Paul Lieberman
*Assistant Examiner*—William S. Parks
*Attorney, Agent, or Firm*—Charles J. Zeller

[57] ABSTRACT

A process for dyeing hair by preparing and thereafter applying to the hair an aqueous reaction medium comprising dopa and an oxidant selected from ferricyanide and permanganate salts, said aqueous reaction medium further containing a buffer to maintain the pH in the range from 6 to 10 during the reaction, and removing said aqueous reaction medium from the hair within about one hour following its preparation

43 Claims, No Drawings

PROCESS AND KIT FOR DYEING HAIR

FIELD OF THE INVENTION

The present invention relates to the use of dopa to generate melanin to dye hair permanently. More specifically, the present invention relates to a hair dyeing process wherein dopa and oxidant react in an aqueous environment to provide unexpectedly high 5,6-dihydroxyindole concentrations in the aqueous environment, the 5,6-dihydroxyindole formed during the reaction being effective to dye hair permanently upon its coincident conversion to melanin while in the hair. Furthermore, the present invention concerns a method of dyeing hair wherein the melanin is generated by the user from separately packaged reactants sold in the form of a kit.

BACKGROUND OF THE INVENTION

As reported, for example, in Prota, *Progress in the Chemistry of Melanins and Related Metabolites*, Med. Res. Reviews, 8:525–56 (1988), melanins are naturally occurring pigments present in hair and skin. In humans biosynthesis takes place in tyrosinase containing melanocytes. The tyrosinase enzyme catalyzes the hydroxylation of tyrosine to dopa and its subsequent oxidation to dopachrome. Once formed, dopachrome undergoes a series of complex reactions in the formation of eumelanins and phaeomelanins. Eumelanins provide black and brown pigments, and are formed by oxidative polymerization of 5,6-dihydroxyindole derived biogenetically during the melanogenesis. On the other hand, phaeomelanins provide yellow to reddish brown pigmentation to hair, and are formed by oxidative polymerization of cystein-S-yl-dopas via 1,4-benzothiazine intermediates.

Synthetic 5,6-dihydroxyindole (DHI) has been disclosed in the prior art for use in hair and skin dyeing. For example, U.S. Pat. No. 2,934,396 to Charle discloses a process for dyeing hair by contacting hair with an aqueous solution of DHI having a pH of at most 7 for 5 to 60 minutes, followed by an application of an aqueous solution capable of inducing oxidation and/or polymerization of DHI.

Dopa and dopamine are disclosed as hair dyeing precursors in the process of Herlihy, U.S. Pat. No. 4,746,322, wherein the aqueous hair dyeing composition comprises said precursor, an organic compound to assist dye dispersion and an iodate or periodate. The dopa or dopamine dye precursor is present in the aqueous hair dye composition in an amount of from about 1 to about 100 mg/ml, preferably from about 5 to about 25 mg/ml. Dopamine is preferred, according to Herlihy. The iodate or periodate is present in the composition at a concentration of 1 to about 50 mg/ml, while the dispersing agent is present in an amount of from about 0.1 to 30% (wt./vol.). Optionally, a color modifier can be incorporated into the aqueous composition of Herlihy, at a level of from about 0.1 to about 10 mg/ml. pH may be maintained between about 3 to about 7 by incorporation of an effective amount of a buffer. According to Herlihy, the above-described aqueous compositions disperse the dye on the hair shaft "with little or no penetration into the hair shaft." Column 2, lines 56–58.

The prior art fails to provide a commercially feasible process for effectively, permanently dyeing hair using dopa as a starting reagent. It is believed this failing is attributable to an inability of the prior art processes in making 5,6-dihydroxyindole available on the hair at concentrations suitable for its diffusion into the hair, for subsequent conversion to nondiffusable melanin, as further explained in detail below.

Indeed, the inability to provide an inexpensive yet effective process for dyeing hair with a melanin precursor has prevented use of melanogenesis in the commercial dyeing of hair.

Notwithstanding such inability, interest in melanogenesis to dye hair remains quite high. This is because synthetic melanin pigments provide an exceptionally natural-looking brown or black color. Moreover, they are not irritating to the skin. Nor are they mutagenic. Accordingly, the hair dyeing art has long awaited the present invention—a process for permanently dyeing hair with synthetic melanins that is economically viable—and represents a major advance in the art.

It has now been found, quite surprisingly, that an aqueous hair dyeing process wherein an effective melanin-forming hair dyeing amount of 5,6-dihydroxyindole is generated during the reaction of dopa with an oxidant can be practiced inexpensively and under commercially feasible conditions, to achieve a permanent hair color.

SUMMARY OF THE INVENTION

The hair dyeing process of the present invention contemplates the preparation of an aqueous hair dyeing composition containing 5,6-dihydroxyindole (DHI), and applying the aqueous composition to the hair, the DHI provided by the aqueous composition being capable of diffusing into the hair shaft and further being in an amount effective to dye hair permanently upon its coincident conversion to melanin while in the hair.

The aqueous hair dyeing composition is produced by reacting dopa or a salt thereof with an inorganic oxidant selected from the group consisting of soluble ammonium, alkali and alkaline earth metal salts, especially sodium and potassium salts, of ferricyanide and permanganate, in an aqueous reaction medium buffered by sufficient buffering agent to maintain the reaction medium pH from about 6 to about 10 throughout the series of reactions that take place, as set forth in greater detail below. Ferricyanide salts are highly preferred.

In order to achieve the permanent dyeing of hair in accordance with the process of the present invention, it is critical to generate melanin from the aqueous DHI-containing hair dye composition in such amount as to effect a color change to the hair. It is further critical that the hair dye composition be applied to the hair prior to the substantial formation of melanin so that the DHI formed during the dopa-oxidant reaction may diffuse into the hair prior to the generation of melanin, the melanin then being formed within the hair. It is additionally critical that the contact time (as hereinafter defined) of the hair dye composition with the hair be less than about one hour.

In another aspect of the present invention, it has been found that the rearrangement of dopachrome, an intermediate leading to the formation of DHI, is hastened by proper selection and amount of the buffer, apart from its requirement for maintaining pH of the reaction medium, and permits the dyeing process to be completed within about one hour. Preferably, the buffer is a phosphate, carbonate or bicarbonate, and typically is included in substantial excess over the amount needed to maintain the requisite pH.

In yet another aspect of the present invention, the process for dyeing hair contemplates treatment of the hair with a solution of a metal ion salt, which treatment accelerates the formation of melanin from DHI. Pretreatment with the metal salt is especially preferred and copper salts are the preferred species.

The process of the present invention may conveniently be practiced by providing premeasured amounts of the reactants in separate containers packaged in kit form. The user simply admixes the reactants on or with subsequent application to the hair and allows the composition while it is reacting to remain on the hair for the prescribed period of time. It is seen that no special expertise is required to carry out the process, and accordingly the product and process is equally suitable for in-home use by the nonprofessional as well as salon use by the professional. Advantageously, the product in kit form is shelf-stable and is therefore suitable for retail sale and without precautions generally required for DHI, such as storage under an inert gas atmosphere.

DETAILED DESCRIPTION OF THE INVENTION

The hair dyeing process of the present invention comprises the preparation of an aqueous hair dyeing composition by reacting dopa and an inorganic oxidant and contacting the hair with said hair dyeing composition for a period of time of about less than one hour, said reaction proceeding in such manner and under such conditions as to provide on the hair an amount of 5,6-dihydroxyindole (DHI) during the period of contact effective to generate a hair dyeing amount of melanin, the DHI diffusing into the hair during the period of contact and forming melanin in situ in the hair to provide a permanent color. By "permanent" is meant a color not removable by shampooing with a conventional surfactant-containing shampoo, the permanency being attributable to the inability of melanin to diffuse from the hair shaft in view of its molecular size. Preferably, the contact time of the hair dyeing composition on the hair is from about 5 to about 45 minutes, most preferably from about 5 to about 30 minutes.

In another aspect of the present invention, the dopa and the oxidant reactants are separately provided in kit form, for admixture by the user to initiate the reaction. It is possible to combine the reactants directly on the hair of the user, but preferable to mix them in a mixing vessel, for subsequent application to hair following commencement of the reaction.

The hair dyeing process involves a series of reactions leading to the formation of 5,6-dihydroxyindole (DHI), a melanin precursor capable of diffusing into the hair shaft. Within the hair shaft, DHI is oxidized by air to melanin, an insoluble polymeric pigment incapable of diffusion into or from the hair shaft. Accordingly, the DHI-containing hair dye composition must be applied to the hair prior to the substantial formation of melanin. Inasmuch as DHI, upon formation, will begin its conversion to melanin by reaction with air, it is critical to apply the reaction medium, essentially unreacted or partially reacted with respect to DHI formation, to hair at or shortly after admixture of the dopa and the oxidant reactants.

The term "applying" as used herein means the contact between the hair dye composition and the hair as described in the two preceding paragraphs. Placing the hair dye composition on the hair following substantial melanin formation is not operable since the insoluble melanin will not diffuse into the hair, and will be largely stripped away during subsequent shampooing. For convenience, a contact time of "less than about one hour" as used throughout this application is measured from the onset of mixing of the dopa and the oxidant reactants.

It should also be understood that a suitable aqueous hair dyeing composition can be obtained without adding additional constituents to the aqueous reaction medium. That is, the aqueous reaction medium and the aqueous hair dyeing composition may be regarded as equivalents, for example, in the case where the reactions involved occur, in whole or in part, upon the hair to be dyed. As described below, however, it is preferred to include additional optional constituents, e.g., thickeners, etc., to provide a more elegant product.

In the process of the present invention, dopa is oxidized to dopaquinone, which spontaneously forms cyclodopa. Additional oxidant further reacts with the cyclodopa to form dopachrome which undergoes spontaneous, although not immediate, transformation to 5,6-dihydroxyindole through rearrangement of the dopachrome species and the release of carbon dioxide. The reactions for the preparation of melanin from dopa in accordance with the present invention are presented below.

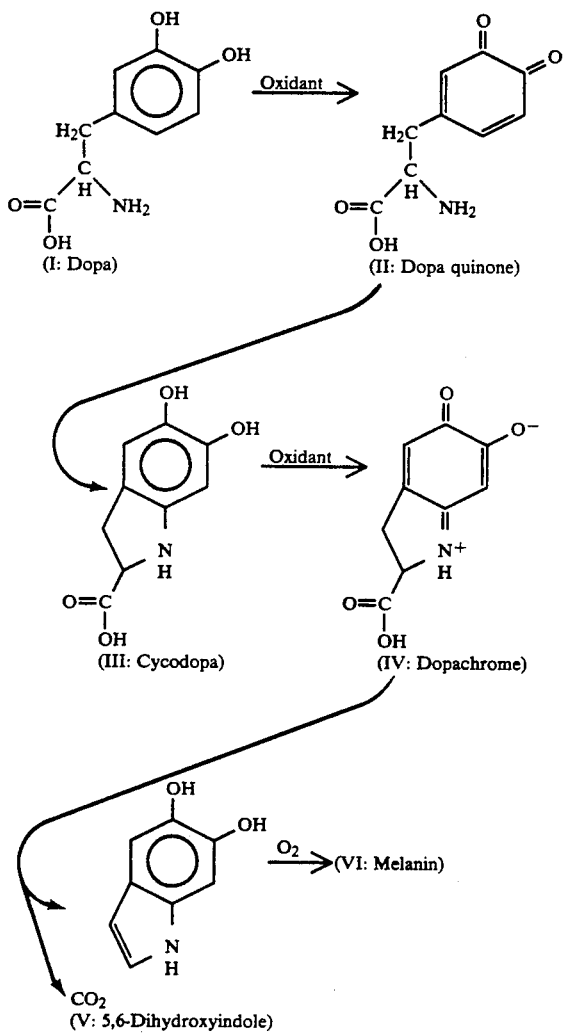

It is seen that the sequence of reactions above is conducive to many possible competing reactions Thus, in the reaction scheme, species II may react with species I as well as forming III; species III may react with species II as well as forming species IV, etc. Because second order reactions are involved, the problem of unwanted competing reactions becomes especially acute as the concentrations of particular reacting species, especially dopa, in solution are high, as in the process of the present invention.

A second difficulty encountered in the process of the present invention is that the rearrangement of dopachrome proceeds slowly. Thus, Napalitano et al, Gaz. Chim. Italiana, 115:357-9 (1985), report a rearrangement time of greater than four hours, far too slow for the aqueous reaction media to be useful as a hair dye product.

The third problem that mitigates against the commercial use of dopa as a starting reagent in the dyeing of hair is that DHI, species V, which oxidizes relatively slowly in air to form melanin, is essentially immediately oxidized by unreacted oxidant to form a polymeric sludge, unsuitable for dyeing hair. This problem exists even though the hair is pretreated with a transition metal salt, since the DHI is prevented from diffusing into the hair.

The present invention overcomes all three problems which prevent the use of dopa as a reactant leading to the formation of 5,6-dihydroxyindole as a melanin precursor in a commercially viable process for permanently dyeing hair By overcoming each of these problems, the present invention achieves a DHI concentration in the aqueous hair dyeing composition that leads to a melanin level effective for permanently dyeing hair, and provides a process that can be practiced by the user in under about 60, preferably under 45, most preferably under 30 minutes.

With regard to the first problem, the present invention contemplates the substantial, rapid conversion of dopa to dopaquinone to cyclodopa and to dopachrome, and without significant loss of yield occasioned by the aforementioned competing reactions. To this end applicants have found that a select group of oxidants is suitable to convert dopa through to dopachrome rapidly and with suppression of the unwanted competing reactions. It is believed the reactions leading to dopachrome take place in under five minutes, and likely take place in less than one minute, especially when the oxidant is a ferricyanide.

With regard to the second problem, the rearrangement of dopachrome to DHI, which is the rate-controlling reaction in the sequence of reactions leading to DHI, can be accelerated by use of particular buffer constituents present in a rate-potentiating concentration.

With regard to the third problem, the process of the present invention limits the amount of oxidant present in the reaction medium relative to dopa such that the oxidant is essentially completely reacted during the reactions leading to dopachrome.

The Dopa Component

As previously indicated, the preparation of the aqueous hair dye composition is by the consumer, who admixes the dopa and oxidant reactants at the time of use. Dopa or a suitable dopa salt species is present in the initial reaction medium at a level suitable to obtain a hair dyeing amount of melanin, which melanin amount, in turn, is dependent on the DHI levels achieved during the period of contact of the hair dyeing composition with the hair.

The required initial dopa concentration in the reaction medium is generally above the solubility limit for dopa in water. Accordingly, an acid or alkaline aqueous premix of dopa can be prepared prior to preparation of the aqueous reaction medium. Alternatively, the more soluble dopa acid or basic salts can be used in the preparation of the aqueous medium. Use of the dopa salt or the use of an acid or alkaline dopa premix allows the otherwise relatively insoluble dopa reactant to go into solution and be available for rapid reaction.

Illustrative of the suitable soluble acid salts of dopa are dopa hydrochloride and dopa sulfate. Dopa hydrochloride is preferred. Among the suitable basic salts of dopa that can be used are the soluble alkali metal salts and the alkaline earth metal salts of dopa. The sodium and potassium salts are preferred. Any inorganic or organic acid or base can be used to adjust the pH of the dopa premix solution, provided that the agent used does not interfere in the reactions. Suitable bases are ammonium and sodium hydroxide and mono-, di- and trialkanolamines, especially ethanolamines. Such acids are hydrochloric, phosphoric, tartaric, citric and lactic acids and their salts. Sodium hydroxide and hydrochloric acid are preferred.

The dopa (or dopa salt) concentration in the initial reaction medium is from about 3 mg/ml up to about the solubility limit of the dopa species in the reaction medium. Preferably, the dopa concentration is from about 5 to about 25 mg/ml in the initial reaction medium, most preferably from about 5 to about 15 mg/ml.

The Oxidant Component

Suitable oxidants for use in the present invention are selected from the group consisting of soluble ammonium, alkali metal and alkaline earth metal salts, especially ammonium, sodium and potassium salts, of ferricyanide and permanganate. A ferricyanide oxidant is preferred from a kinetic standpoint, inasmuch as its reduced form following reaction—ferrocyanide—will not react further in the aqueous system. A permanganate oxidant is less preferred, as its reduced state is a weakly oxidative species. Although this reduced-state oxidative species is considerably less reactive than the oxidant reactant of the present invention, it may nonetheless react with DHI to some extent, thereby forming melanin or melanin-like species outside the hair and hence lowering the overall efficiency of the process.

These oxidants are quite reactive towards the dopa and cyclodopa species present in the reaction medium during the process. Accordingly, in the process of the present invention, dopachrome is rapidly produced, thereby preventing or greatly limiting side reactions among the dopa, dopaquinone, cyclodopa and dopachrome species.

The oxidant reactant is present in the initial reaction medium at a substantially stoichiometric equivalent concentration, as further described below.

During the conversion of dopa to dopachrome, dopa molecules lose four electrons. Accordingly, if an oxidant that gains one electron is employed, four molar equivalents of oxidant are required. An oxidant gaining two electrons will thus be provided in two molar equivalents. Although the conversion of dopa to dopachrome occurs rapidly, it might be possible to add oxidant slowly or in stages during the reaction. However, this would be difficult and inconvenient for the consumer, and may inadvertently result in oxidant being present during the DHI formation. A greater than about a stoichiometric equivalent amount of oxidant relative to dopa is not recommended, as the excess oxidant will react with DHI. Dopa in an excess stoichiometric equivalent amount relative to oxidant is preferred to ensure that unreacted oxidant does not remain following the reaction. An excess of dopa does not appear to affect the process performance, although unreacted dopa will, of course, reduce the overall efficiency of the process. Generally, the stoichiometric equivalent ratio on a molar basis of dopa to oxidant initially present in the reaction medium will be from about 1.25:1 to 0.95:1, preferably from about 1.1:1 to 1:1, most preferably from about 1.05:1 to 1.01:1.

The Buffering Agent Component

Inasmuch as the pH of the reaction medium will fall during the reactions, it is necessary to provide a sufficient amount of a buffering agent in the reaction medium to maintain the requisite pH. In the process of the present invention, it is critical to maintain the pH of the aqueous reaction medium between about 6 to 10 during the dopa oxidation and dopachrome rearrangement reactions. Preferably, the pH is between about 7 to about 8.5, and especially alkaline to about 8.5.

In addition to controlling reaction medium pH within the aforesaid limits, the buffers and their concentration in the reaction medium employed in the process of the present invention are selected to potentiate the rearrangement of dopachrome to DHI. Thus, as buffer concentration in the reaction medium increases, the time for dopachrome rearrangement decreases. Typically, the buffer is present in an amount in excess of that needed to buffer the reaction mixture. Preferably, then, it is desirable to provide 2 to 25 times, especially 5 to 20 times, as much of these particular buffers as would be needed merely to maintain the reaction mixture pH within the prescribed limits.

Buffers found to be suitable for use in this invention are ammonium and alkali metal phosphates, bicarbonates, carbonates and, to a lesser extent, borates. Also suitable are aminic buffers such as N-[2-hydroxyethyl]-piperazine-N'-[2-ethanesulfonic acid] (HEPES), N-[2-acetamido]-2-aminoethane sulfonic acid (ACES), tris[-hydroxymethyl]aminomethane (TRIZMA) and N-tris[-hydroxymethyl]-methyl-3-aminopropane sulfonic acid (TAPS). Even though not typically employed in the stated pH range, ammonium and alkali metal carbonates and bicarbonates are also suitable.

While the above buffers all regulate pH as required, the choice of particular buffer depends in some instances on the oxidant used to obtain the desired rearrangement rate acceleration. Thus, it has been found that phosphate, carbonate, bicarbonate and the various aminic buffers are especially suitable when the oxidant is ferricyanide. Similarly, the phosphate buffer is preferred when permanganate oxidant is used. The preferred oxidant-buffer systems used in the practice of the present invention are ferricyanide with carbonate, bicarbonate or phosphate and permanganate with phosphate. Other combinations may be useful, and can be determined by experimentation well within the skill of the ordinary practitioner. In this regard, reference is made to the examples.

The Process Parameters

It should be understood that the ability to obtain the necessary DHI concentration depends on both the DHI yield and the amount of dopa available for conversion. Thus, a lower DHI yield would be acceptable when a high initial dopa concentration is provided in the reaction medium. Conversely, a high DHI yield would need to be achieved if a low initial dopa concentration is used.

In the present invention for permanently dyeing hair, DHI is converted to melanin in situ while the hair dyeing composition is in contact with the hair. Thus, the process should be viewed as a dynamic one in which the dopachrome to DHI reaction and the DHI to melanin reaction proceed simultaneously. Accordingly, the concentration and molar yield of DHI based on dopa formed in the hair dye composition is not directly measurable unless the subsequent melanin-forming reaction is prevented. Similarly, amount and yield of melanin is not easily quantitatively measurable because it is formed in the hair. On the other hand, the effectiveness of the process may be determined by measuring the change in hair color when a hair swatch is treated in accordance with the process. Further, such evaluation is an indication of the amount of melanin that has formed in the hair shaft, and hence the amount of DHI that has diffused into the hair shaft during the treatment. The test procedure is discussed further below.

As a guide to the successful practice of the invention, Applicants have found that a perceptible color change to hair occurs within one hour of application to the hair when a peak DHI concentration obtained in the hair dyeing composition is at least about 1.5 mg/ml. This peak DHI concentration, which may be regarded as a practical minimum, occurs typically during the early stage of the reactions described above, normally within the first 30 minutes, preferably within the first 20 minutes of reactant admixture. An initial dopa concentration of about 3 mg/ml, coupled with DHI molar yield of about 50%, is suitable to achieve the practical minimum peak DHI level in the aqueous composition. It should be understood that the peak DHI concentration is measured during the reactions occurring in the reaction medium and in isolation from the hair, as set forth, for example, in Examples 1-11. As measured by HPLC, molar yields of DHI in accordance with the present invention are typically from about 50 to about 70%, with molar yields of the by-product dihydroxyindole carboxylic acid being from about 7 to 9%, both yields being based on conversion of dopa.

Preferably, the peak DHI concentration obtained in the aqueous composition is above about 2.5 mg/ml, most preferably above about 4 mg/ml. DHI molar yields above about 50% and initial dopa concentrations from about 5 mg/ml to the solubility limit in the reaction medium of the dopa species employed are preferred to establish levels of DHI in the hair dye composition suitable to generate a hair dyeing amount of melanin. As a practical matter, peak DHI levels above 12 mg/ml have been difficult to achieve consistently.

Systems wherein the DHI molar yield and the initial dopa concentration cooperatively provide peak DHI concentrations of more than about 2.5 mg/ml are especially suitable to effect a color change in one treatment in accordance with the present invention, while systems that provide peak DHI concentrations of less than about 2.5 mg/ml are particularly useful to color hair gradually over successive treatments in accordance with the disclosed process. Typically, 2 to 14 successive treatments for shorter time periods (less than about 10 minutes) are used to color hair gradually.

In the practice of the present invention, the user is provided with two or more containers of reactant-containing solutions, and with printed instructions to mix the solutions in order to form the hair dye composition and to apply the dye composition to the hair for a period of less than about one hour. The process is generally conducted at room temperature, although elevated temperatures obtained by means of a hair dryer, especially in a hair salon. The user may also place a cap over the hair following the application of the dye composition to the hair, body heat being retained within the cap. Following completion of the contact step, the hair is shampooed to remove excess composition including surface melanin from the hair.

The Hair Dyeing Kit Product

The kit provided in accordance with this aspect of the invention comprises a sufficient amount of buffer, a first container containing a dopa solution, and a second container containing an oxidant solution. The buffer may be individually packaged in a third container, may be present in the first container, or may be present in the second container. When the dopa solution is provided in the form of its acid or basic salt, or is acidic or basic in pH, the buffer would not be present therein. While the kit may contain packets containing amounts, preferably premeasured, of dry powders for preparation of these solutions, it is more convenient to provide them as solutions. Moreover, solutions containing premeasured quantities of the constituents facilitates their correct use by the consumer.

One or more additional containers may be provided in the kit, as described below with regard to optional constituents. The optional constituents may also be contained within the solutions, barring any incompatibility.

The consumer admixes the components of the kit, suitably as the aqueous solutions or as dry powders and water, according to written instructions, to obtain the aqueous reaction mixture. The admixture may be conducted in a separate vessel supplied with or external to the kit, or may take place in a container of the kit adapted to provide sufficient head space for mixing. The reactants may also be admixed on the hair of the user. Essentially upon mixing, reaction of dopa will commence. The DHI formed will subsequently oxidize in air to form melanin, visually indicated by the formation of color. The reacting mixture is applied to the hair, the completion of the DHI reaction taking place on the hair, with concurrent diffusion of DHI (and/or partially oxidized DHI) into the hair where it is oxidized essentially to completion to form melanin, whereby a permanent hair color is obtained. After the desired hair shade is reached, most preferably within about 30 minutes, the hair dye composition that was applied to the hair is removed, preferably with a conventional shampoo.

Because the hair dye composition is applied to the hair initially or shortly after the reactions commence, the reaction time for melanin formation and the contact time on the hair are essentially the same. The kinetics of melanin formation contemplated by the present invention are such that the reaction should take place within the prescribed contact time constraints previously described. However, failure to remove the hair dyeing composition within the prescribed contact time is not consequential, as no appreciable further hair color change will occur.

Hair Treatment With Metal Ions

It is also known that certain transition metal and zinc ions, for example, copper, zinc, nickel, cobalt and iron ions, accelerate the oxidation of DHI to melanin. As used herein "transition metal" is deemed to include zinc. Solutions of the salts of these ions applied to hair in conjunction with the application of the dye composition of this invention to hair result in a deepening of the color obtained. The transition metal salt ions effect a color change to the hair more rapidly than when they are not used. Typically, the color change is obtained in less than about 30, preferably less than about 15, minutes. Because the DHI that is formed is used more efficiently, peak DHI concentrations of above 1.5 mg/ml are also generally useful in obtaining significant color in a single treatment.

Preferably, the metal salt solution is applied as a pretreatment to the hair for a predetermined period of time, typically for about 1 to about 10 minutes, excess metal salt then being removed from the surface of the hair by rinsing or shampooing prior to the application of the hair dye composition. It is preferable to incorporate the metal ions into a shampoo formulation, in which event a water rinse will suffice to remove the excess. The metal ions are believed to penetrate into the hair shaft and thus be available to rapidly accelerate the conversion of diffused DHI to melanin upon subsequent treatment with the hair dye composition described herein. The metal salt solution typically contains from about 0.01 to about 1% of the metal salt, and may further contain other adjuvants, such as thickener, surfactant, and the like, e.g., as noted below for the hair dye composition. For best results the metal salts should be soluble in the aqueous vehicle used in the treatment. Preferably, the aqueous vehicle is alkaline, but this is not essential Copper II salts are preferred.

Accordingly, the kit containing the first and second premixes may also contain a separately packaged solution of these metal salts. The use of metal salts to enhance the hair color obtained with DHI is described in detail in British Patent No. 2,132,642, incorporated herein by reference thereto.

Optional Constituents

The variously described embodiments of the present invention may also include in the hair dye composition one or more optional ingredients, which may be provided in one or more additional containers of the kit for admixture by the user into the aqueous reaction mixture, or, if compatible, may be incorporated into the oxidant or dopa premix solutions described previously.

Well-known conventional additives usually employed in oxidative hair coloring compositions such as organic solvents, thickeners, surface-active agents, pH adjusting agents, antioxidants, fragrances and chelating agents may be included in the compositions of the inventions.

The hair dye compositions used in the process of the present invention can include an organic solvent as a cosolvent. The organic solvent may assist in the dissolution of the components of the composition, and is present typically in an amount up to about 30%, preferably up to about 15%. A desirable range is from about 0.1 to about 15%, most preferably from about 1 to 10%. Suitable solvents are mono- and polyhydric alcohols, for example, ethyl alcohol, isopropyl alcohol, propylene glycol, benzyl alcohol, etc., and glycol ethers, such as 2-butoxyethanol, ethylene glycol monoethyl ether and diethyleneglycol monoethyl ether.

Surface-active agents employed in the dyeing compositions of this invention can be anionic, nonionic, cationic, amphoteric or zwitterionic. By way of examples of the various types of surface-active agents, there can be mentioned: higher alkylbenzene sulfonates; alkyl-naphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester, myristyl sulfate; glyceryl monostearate; triethanolamine oleate, sodium salt of palmitic methyl taurine; cetyl pyridinium chloride; lauryl sulfonate; myristyl sulfonate, lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; triethanolamine salt of p-dodecylbenzene sulfonate; nonylaphthalene sodium sulfonate; dioctyl sodium sulfosuccinate; sodium N-methyl-N-oleoyl taurate; oleic acid ester, of sodium isothionate; sodium dodecyl sulfate; the sodium salt of 3-diethyl: tridecanol-6-sulfate and the like. The quantity of surface-active agent can vary over a wide range, such as from about 0.05% to 15% and preferably from about 0.10 to 5% by weight of the composition. The anionic and nonionic surfactants are employed typically as emulsifiers, while the cationic surfactants are useful to impart a hair conditioning benefit to the hair. Care must be exercised when anionic and cationic surfactants are both incorporated, in view of possible incompatibility.

Chelating and sequestering agents include, for example, ethylenediaminetetraacetic acid, sodium citrate, etc., and are present in an amount of under about 1%.

A thickening agent may also be incorporated in the dyeing composition of this invention, which may be one or several of those commonly used in hair dyeing. These are exemplified by such products as sodium alginate or gum arabic, or cellulose derivatives, such as methylcellulose, e.g., Methocel 60 HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.1 to 5% by weight of the composition. The viscosity of the composition may vary from about 1 cp to about 100,000 cps. For a typical lotion formulation, composition viscosity is between about 100 cps to about 10,000 cps, at which viscosity the composition can be applied to the hair without running or dripping.

The composition of the present invention may also include pH adjustment agents to provide an initial reaction medium pH within the previously stated range. Typically, these pH adjustment agents are incorporated into the dopa premix, as previously described, to ensure dissolution of the dopa. However, such pH adjustment agents may also be incorporated into the oxidant premix or directly into the aqueous reaction medium. Typical pH adjustment agents have been described in the section entitled The Dopa Component.

In alkaline solution the dopa salt may be somewhat susceptible to oxidation, for example, by air entrapped in an alkaline dopa premix solution. Accordingly, a small amount of an antioxidant may be included in the alkaline dopa premix. In such instances the amount of oxidant in the oxidant premix might be increased to neutralize the antioxidant upon admixture of the dopa and the oxidant premixes.

This list of optional ingredients is not intended as limiting. Other suitable adjuvants for inclusion in the hair dye composition are recited, for example, in Zviak, *The Science of Hair Care* (1986) and Balsan and Sagarin, Cosmetics: Science and Technology, Vol. 2 (Second Edition 1972).

The invention is now illustrated by the following examples. Unless otherwise indicated, concentrations and ratios in the specification including the examples are on a weight basis by weight of the total composition.

EXAMPLES 1-9

15 ml of a 0.1M solution of dopa (pH about 1.9) was prepared by dissolving dopa in 0.1M hydrochloric acid. Also prepared was a 0.36M solution of potassium ferricyanide also containing a buffer. To form the aqueous reaction medium, equal volumes of the dopa and the oxidant-buffer premixes were combined in a vessel that was open to the atmosphere. The buffer and its concentration in the aqueous reaction medium is indicated in Table I. Initial pH values of the reaction medium were measured as noted in Table I. The 5,6-dihydroxyindole concentration was measured at 15 minutes following mixing of the premixes, as set forth in Table I, using HPLC techniques known in the art.

TABLE I

| Example | Buffer | Buffer Conc. | pH (immediately after mixing) | DHI Conc. at t = 15 Min. (mg/ml) |
|---|---|---|---|---|
| 1 | Potassium phosphate | 0.36 M | 6.7 | 4.3 |
| 2 | Potassium phosphate | 0.59 M | 6.8 | 4.5 |
| 3 | Sodium bicarbonate | 0.70 M | 7.0 | 4.6 |
| 4 | Sodium borate | 0.50 M | 7.1 | 1.6 |
| 5 | HEPES | 0.33 M | 7.0 | 3.2 |
| 6 | ACES | 0.33 M | 7.1 | 3.4 |
| 7 | TRIZMA | 0.33 M | 7.5 | 4.8 |
| 8 | TAPS | 0.23 M | 7.7 | 3.4 |
| 9 | TAPS | 0.33 M | 7.6 | 4.1 |

The data in Table I shows that Examples 1-3 and 5-9 each produced after 15 minutes a DHI concentration well above the minimum peak concentration of 1.5 mg/ml required for a DHI-containing hair dye composition. Example 4, in which sodium borate was used as the buffer, achieved a 1.6 mg/ml DHI level after 15 minutes at the 0.50M buffer concentration (based on the oxidant premix) employed. Examples 1, 2, 8 and 9 indicate that DHI concentration is a function of buffer concentration. The levels of buffer employed in each of these examples were well above the buffer concentration needed to maintain reaction mixture pH in the range of 6 to 10.

EXAMPLE 10

15 ml of a 0.16M dopa solution (pH 1.9) was prepared as a premix by dissolving dopa in 0.16M hydrochloric acid. A 0.21M solution of potassium permanganate was prepared as the oxidant premix, and included potassium phosphate as the buffering agent. Equal volumes of the dopa premix and the oxidant were combined to form the aqueous reaction medium, which had an initial pH of 6.8. The aqueous reaction medium contained a 0.428M concentration of said buffering agent. The DHI concentration was 2.1 mg/ml after 5 minutes and 1.5 mg/ml after 15 minutes.

EXAMPLE 11

0.15 g dopa was dissolved in 7.5 ml 0.1M hydrochloric acid to form the dopa premix. An oxidant premix containing 0.9 g potassium ferricyanide, 0.75 g sodium bicarbonate and 7.5 ml water was prepared and rapidly mixed with the dopa premix to form the aqueous reaction medium. The pH of the aqueous reaction medium immediately after formation was 6.9. DHI concentrations were determined by HPLC analysis on aliquots of the reaction medium after 5 and 25 minutes. After 5 minutes the DHI concentration as 1.75 mg/ml, and after 25 minutes the DHI concentration was 6.4 mg/ml.

EXAMPLE 12

The ability for an aqueous composition containing dopa and a periodate to form DHI based on the teachings of U.S. Pat. No. 4,746,322 to Herlihy was investigated.

A dopa premix comprising 0.15 g dopa, 0.3 g benzyl alcohol and 10 ml water was prepared by admixture of these ingredients in an open breaker with stirring for about five minutes. 60 mg sodium periodate was then added, with adjustment of the pH to 5.0 with the addition of dilute hydrochloric acid. Aliquots of the solution were removed after 5, 25 and 45 minutes and tested for DHI presence using HPLC techniques. None of the aliquots contained a registrable level of DHI (i.e., less than 0.1 mg/ml DHI).

The experiment was repeated using 60 mg sodium iodate as the oxidant. Again, HPLC analysis failed to show registrable levels of DHI after 5, 25 and 45 minutes.

EXAMPLE 13

This Example illustrates the dyeing of hair in accordance with the process of the present invention using a reaction medium containing potassium ferricyanide as the oxidant and sodium phosphate as the buffer.

A dopa premix was prepared by adding 0.15 g dopa to 7.5 ml 0.1M hydrochloric acid. An oxidant premix comprising 0.9 potassium ferricyanide, 1.45 g sodium phosphate (1.15 g $Na_2HPO_4$ and 0.3 g $Na_3PO_4 12H_2O$) and 7.5 ml water was prepared, and rapidly admixed with the dopa premix to provide the aqueous reaction medium, which had an initial pH of 7.2.

A swatch of virgin gray hair was contacted with the aqueous reaction medium for 30 minutes, rinsed with water, shampooed and dried.

The color profile of the virgin and treated hair was evaluated using the Hunter Tristimulus method, which method is well known in the art. In the Hunter method, the parameters a and b may be positive or negative and define the chromatic condition of the hair. Thus, the more positive the a value, the greater the redness of the hair, while the more negative the a value, the greater the greenness of the hair. Similarly, positive b values indicate yellowness, while negative b values indicate blueness. More importantly, the L parameter is a measure of color intensity, and has a value of 0 for absolute black to 100 for absolute white. Generally, hair having an L value of about 15 or less is considered black, while an L value of about 60 is white. It should be understood that the L value scale is not linear, but rather is sigmoidal. Proximate to 0 and proximate to 100 hair color intensity varies minimally with unit changes in the L value. Between L values of about 20 to about 50, hair color intensity varies significantly with unit changes in L value. Thus, the Hunter values are more sensitive in the region where the human eye is able to perceive color changes.

The before and after Hunter values are as follows:

|  | L | a | b |
| --- | --- | --- | --- |
| Before dyeing (Virgin Hair) | 38.0 | −0.4 | 7.7 |
| After dyeing | 30.4 | 0.3 | 5.3 |

It is seen that the Virgin gray hair was made several shades darker when treated in accordance with the process of the present invention.

EXAMPLE 14

The process of Example 13 was repeated, except that the swatch of virgin gray hair (L=38.0, a=−0.4, b=7.7) was first pretreated for 5 minutes with an alkaline shampoo containing conventional anionic surfactants and further containing 0.08M copper sulfate, rinsed thoroughly, and contacted for 30 minutes with the aqueous reaction medium described above. The hair was dyed black (L=16.5, a=0.6, b=1.3).

EXAMPLE 15

This Example illustrates the dyeing of hair in accordance with the process of the present invention using a reaction medium containing potassium ferricyanide as the oxidant and sodium bicarbonate as the buffer.

A dopa premix was formed by adding 0.15 g dopa to 7.5 ml 0.1M HCl. The oxidant premix contained 0.9 g potassium ferricyanide, 0.87 g sodium bicarbonate and 7.5 ml water, and was admixed rapidly with the dopa premix. The initial pH of the thus formed aqueous reaction medium was 7.1.

Virgin gray hair (as in Example 13) was contacted for 30 minutes, rinsed, shampooed and dried. The Hunter values for the hair dyed in this manner were L=25.6, a=0.5 and b=3.7.

EXAMPLE 16

The process of Example 15 was repeated but with a virgin gray hair swatch that was first treated for 5 minutes with the copper-containing shampoo described in Example 14. The swatch was dyed black (L=14.2, a=0.3 and b=0.6).

EXAMPLE 17

The process of Example 14 was repeated, except that the aqueous reaction medium was in contact with the swatch for only 10 minutes. The hair was dyed black (L=15.6, a=0.6 and b=1.1).

EXAMPLE 18

The process of Example 14 was repeated except the oxidant premix contained 1.4 g sodium phosphate as the buffer, and further contained 1.79 g sodium citrate to adjust the pH. The initial reaction medium pH was 9.6 and the contact time of the reaction medium with hair was 15 minutes. The hair was dyed black (L=13.7, a=0.4 and b=0.2).

EXAMPLE 19

The process of Example 14 was repeated except that the buffer was 0.6 g tris(hydroxymethyl)aminomethane. The initial pH was 7.5. The hair was dyed black (L=13.0, a=0.3 and b=0.3).

EXAMPLE 20

A dopa premix was made by adding 0.15 g dopa to 7.5 ml 0.1M HCl. The oxidant premix contained 0.15 g potassium permanganate, 1.1 g sodium phosphate (0.8 g $Na_2HPO_4$ and 0.3 g $NaH_2PO_4\ H_2O$) and 7.5 ml water. Initial reaction medium pH was 7.3.

A swatch of virgin gray hair (L−37.9, a=−0.2 and b=8.5) was dyed by contacting the swatch with the aqueous reaction medium for 30 minutes. The swatch was several shades darker in color (L =33.8, a=−0.2 and b=6.7).

EXAMPLE 21

The process of Example 20 was repeated, but with a five-minute pretreatment with the copper shampoo. The hair was dark brown (L=21.8, a=−0.2 and b=2.1).

EXAMPLE 22

The process of Examples 20 and 21 were repeated, but without the phosphate buffer in the aqueous reaction medium. The initial pH was about 7.9. After contact for 30 minutes, L=38.0, a=0.5 and b=7.9. With copper shampoo pretreatment for 5 minutes and contact for 30 minutes with the reaction mixture, L 28.9, a=−0.8 and b=4.2. Neither treatment method provided the same level of dyeing as the analogous process of the present invention

We claim:

1. A method for permanently dyeing hair with a melanin precursor comprising the steps of:
   (a) oxidizing dopa or an acid or basic salt thereof with an oxidant selected from the group consisting of soluble ammonium, alkali metal and alkaline earth metal ferricyanide and permanganate salts in an aqueous reaction medium containing a buffering agent to form dopachrome, the dopachrome rearranging to form 5,6-dihydroxyindole, the concentrations of the dopa and the oxidant reactants being in amounts effective to provide a hair coloring concentration of the 5,6-dihydroxyindole in the aqueous reaction medium, said aqueous reaction medium being substantially free of said oxidant reactant prior to the substantial formation of 5,6-dihydroxyindole, and said buffering agent being present in the aqueous reaction medium in an amount sufficient to maintain its pH between about 6 to about 10 during the oxidation and rearrangement reactions, the buffer selection and concentration further being adapted to potentiate the rearrangement of dopachroma to 5,6-dihydroxyindole;
   (b) contacting the hair with the aqueous reaction medium and allowing the 5,6-dihydroxyindole to diffuse into the hair in an amount sufficient to generate a hair coloring amount of melanin;
   (c) permanently coloring the hair by allowing the 5,6-dihydroxyindole present in the hair to form melanin, and
   (d) removing excess aqueous reaction medium from the hair within about one hour on onset of the dopa-oxidant reaction.

2. The method of claim 1 wherein the dopa species is present in the reaction medium initially at a concentration of at least about 5 mg/ml, and wherein the dopa to oxidant stoichiometric equivalent ratio in the initial reaction medium is from about 1.25:1 to about 0.95:1.

3. The method of claim 2 wherein the buffering agent is selected from the group consisting of ammonium, sodium and potassium salts of phosphates, carbonates, bicarbonates and borates, and aminic buffers.

4. The method of claim 3 wherein the peak 5,6-dihydroxyindole concentration is at least about 1.5 mg/ml, as measured during the reactions occurring in the reaction medium and in isolation from the hair.

5. The method of claim 1, 2 or 4 further comprising the steps of first applying to the hair a pretreatment solution containing an effective amount of a metal ion that promotes melanin formation, and thereafter removing the excess metal ion from surface of the hair.

6. The method of claim 5 wherein the metal ion is present in the pretreatment solution in an amount of from about 0.001 to about 1% by weight of said solution, and wherein the metal ion is selected from the group consisting of copper, zinc, nickel and iron.

7. The method of claim 6 wherein the oxidant is ferricyanide, and wherein the buffer is selected from the group consisting of potassium or sodium phosphate, carbonate and bicarbonate.

8. The method of claim 6 wherein the oxidant is permanganate and the buffer is potassium or sodium phosphate.

9. The method of claim 6 wherein the metal ion is copper II.

10. The method of claim 6 wherein said peak 5,6-dihydroxyindole concentration is obtained within about 30 minutes from the onset of the dopa-oxidant reaction.

11. The method of claim 6 wherein the peak 5,6-dihydroxyindole concentration is above about 2.5 mg/ml, as measured during the reactions occurring in the reaction medium and in isolation from the hair.

12. The method of claim 11 wherein the buffering agent is present in an amount of at least twice that needed to maintain the pH of the reaction medium between about 6 to about 10.

13. The method of claim 4 wherein oxidant is ferricyanide, and wherein the buffer is selected from the group consisting of potassium or sodium phosphate, carbonate and bicarbonate.

14. The method of claim 4 wherein the oxidant is permanganate and the buffer is potassium or sodium phosphate.

15. The method of claim 13 or 14 wherein the peak 5,6-dihydroxyindole concentration is at least about 2.5 mg/ml, as measured during the reaction occurring in the reaction medium and in isolation from the hair.

16. The method of claim 15 wherein the peak 5,6-dihydroxyindole concentration is obtained within about 30 minutes from the onset of the dopa-oxidant reaction.

17. The method of claim 13 or 14 wherein the peak 5,6-dihydroxyindole concentration is between about 4 to about 12 mg/ml, as measured during the reactions occurring in the reaction medium and in isolation from the hair.

18. The method of claim 3 wherein the peak 5,6-dihydroxyindole concentration is at least about 2.5 mg/ml, as measured during the reactions occurring in the reaction medium and in isolation from the hair, and is obtained within about 30 minutes from the onset of the dopa-oxidant reaction.

19. The method of claim 18 wherein the buffering agent is present in an amount of at least twice that needed to maintain the pH of the reaction medium between about 6 to about 10.

20. The method of claim 12 wherein the dopa to oxidant stoichiometric equivalent ratio in the initial reaction medium is from about 1.1:1 to about 1:1.

21. The method of claim 20 wherein the pH of the reaction medium is maintained between about 7 to about 8.5.

22. The method of claim 19 wherein the dopa to oxidant stoichiometric equivalent ratio in the initial reaction medium is from about 1.1:1 to about 1:1.

23. The method of claim 22 wherein the pH of the reaction medium is maintained between about 7 to about 8.5.

24. The method of claim 4 wherein each of the dopa and the oxidant are provided in an aqueous solution, the solution of said oxidant and the solution of said dopa being combined to form said reaction medium.

25. The method of claim 24 wherein dopa is present in the aqueous media in the form of an acid salt.

26. The method of claim 25 wherein the dopa is dopa hydrochloride, dopa sulfate, and mixtures thereof.

27. The method of claim 24 wherein dopa is present in the aqueous media in the form of a basic salt.

28. The method of claim 27 wherein the dopa is sodium or potassium dopa and mixtures thereof.

29. The method of claim 24 wherein the buffering agent is contained in the oxidant solution.

30. The method of claim 24 wherein the buffering agent is present in an amount of at least twice that needed to maintain the pH of the reaction medium between about 6 to about 10.

31. A hair dyeing kit for permanently dyeing the hair with melanin formed from 5,6-dihydroxyindole, which includes in a single package a plurality of containers, the kit comprising (a) a first container containing an aqueous solution of a dopa or an acid or alkaline salt thereof; (b) a second container containing an oxidant selected from the group consisting of water-soluble ammonium, alkali metal and alkaline earth metal salts of ferricyanide and permanganate, the amount of oxidant contained in said container being an essentially stoichiometric equivalent amount with respect to dopa contained in the first container, and (c) a buffering agent selected from the group consisting of ammonium and alkali metal salts of phosphates, carbonates, bicarbonates and borates, and aminic buffers, the amount of buffering agent contained in the kit being sufficient to provide a pH of from about 6 to about 10 when admixed with the contents of the first and the second containers and further to potentiate the formation of 5,6-dihydroxyindole, the concentration of the dopa present in the kit being in an amount effective to provide a hair coloring concentration of the 5,6-dihydroxyindole.

32. The hair dyeing kit of claim 31 wherein the dopa is dopa hydrochloride, dopa sulfate and mixtures thereof.

33. The hair dyeing kit of claim 31 wherein the dopa is sodium or potassium dopa.

34. The hair dyeing kit of claim 31 wherein the oxidant is potassium ferricyanide and the buffering agent is selected from the group consisting of ammonium, sodium or potassium salts of phosphates, carbonates and bicarbonates.

35. The hair dyeing kit of claim 31 wherein the oxidant is potassium permanganate and the buffer is potassium or sodium phosphate.

36. The hair dyeing kit of claim 31 wherein the dopa and oxidant components in the kit are present in a dopa to oxidant stoichiometric equivalent ratio of from about 1.25:1 to about 0.95:1.

37. A method of permanently dyeing hair using the kit of claim 31 comprising forming with the buffer a admixture of the dopa and oxidant solutions to obtain a hair dye composition, applying said composition to hair, allowing said composition to color the hair permanently, the composition being in contact with the hair for less than about one hour, and removing the composition from the hair.

38. The method of claim 37 wherein the oxidant is ferricyanide and the buffer is selected from the group consisting of ammonium, sodium and potassium salts of bicarbonates, carbonates and phosphates.

39. The method of claim 37 wherein the oxidant is permanganate and the buffer is potassium or sodium phosphate.

40. The method of claim 38 or 39 wherein the hair is rinsed with water within 30 minutes following application of the composition to the hair.

41. The method of claim 40 wherein the buffer is present in the admixture in an amount of at least twice that needed to maintain the pH between about 6 to about 10.

42. The method of claim 37, 38 or 39 further comprising the step of applying to the hair an alkaline solution containing a metal ion that promotes melanin formation from the 5,6-dihydroxyindole present in the hair dyeing composition.

43. A method for permanently dyeing hair with a melanin precursor comprising the steps of:
(a) reacting dopa or an acid or basic salt thereof and a soluble ammonium, alkali metal or alkaline earth metal ferricyanide oxidant in an aqueous reaction medium further containing a buffering agent present in an amount sufficient to maintain the pH of the reaction medium between about 6 to about 10 during the reaction, the concentration of the dopa and the oxidant reactants being in amounts effective to provide a hair coloring concentration of the melanin precursor in the aqueous reaction medium and the buffer selection and concentration further being adapted to potentiate the formation of the melanin precursor, said reaction medium being substantially free of said oxidant prior to the substantial formation of said melanin precursor;
(b) contacting the hair with the aqueous reaction medium and allowing the melanin precursor to diffuse into the hair in an amount sufficient to generate a hair coloring amount of melanin;
(c) permanently coloring the hair by allowing the melanin precursor present within the hair to form melanin, and
(d) removing excess hair dye composition from the hair within about one hour of onset of the dopa-oxidant reaction.

* * * * *